US007196046B2

(12) United States Patent
Cheung et al.

(10) Patent No.: US 7,196,046 B2
(45) Date of Patent: Mar. 27, 2007

(54) HARD SURFACE CLEANER COMPRISING A SUSPENSION OF ALGINATE BEADS

(75) Inventors: Tak Wai Cheung, Bridgewater, NJ (US); Edward Fu, Kinnelon, NJ (US); Pamela A. Boone, Montvale, NJ (US); Steven Wu, West Nyack, NY (US); Benjamin Costa, Nutley, NJ (US)

(73) Assignee: Reckitt Benckiser Inc., Parsippany, NJ (US)

( * ) Notice: Subject to any disclaimer, the term of this patent is extended or adjusted under 35 U.S.C. 154(b) by 0 days.

(21) Appl. No.: 10/789,018

(22) Filed: Feb. 27, 2004

(65) Prior Publication Data

US 2004/0186037 A1 Sep. 23, 2004

Related U.S. Application Data

(63) Continuation-in-part of application No. PCT/GB04/00589, filed on Feb. 17, 2004, and a continuation-in-part of application No. PCT/GB02/03407, filed on Jul. 25, 2002.

(30) Foreign Application Priority Data

Aug. 31, 2001 (GB) .................. 0121111.9
Feb. 22, 2003 (GB) .................. 0304088.8

(51) Int. Cl.
*C11D 3/37* (2006.01)
*C11D 3/14* (2006.01)

(52) U.S. Cl. .................. 510/418; 510/235; 510/236; 510/238; 510/253; 510/268; 510/269; 510/368; 510/426; 510/438; 510/471; 510/477

(58) Field of Classification Search .............. 510/418, 510/235, 236, 238, 253, 268, 269, 368, 426, 510/438, 471, 477
See application file for complete search history.

(56) References Cited

U.S. PATENT DOCUMENTS

| 2,974,134 | A | | 3/1961 | Pollitzer ............... 260/209 |
| 3,219,656 | A | | 11/1965 | Boettner ............... 260/210 |
| 3,598,865 | A | | 8/1971 | Lew ................ 260/210 R |
| 3,640,998 | A | | 2/1972 | Mansfield et al. ....... 260/210 R |
| 3,707,535 | A | | 12/1972 | Lew ................ 260/210 R |
| 3,772,269 | A | | 11/1973 | Lew ................ 260/210 R |
| 3,839,318 | A | | 10/1974 | Mansfield ............ 260/210 R |
| 3,974,138 | A | | 8/1976 | Lew ................. 536/4 |
| 4,129,423 | A | * | 12/1978 | Rubin .................. 510/398 |
| 4,223,129 | A | | 9/1980 | Roth et al. ............... 536/4 |
| 4,528,106 | A | | 7/1985 | Grolitzer ............. 252/8.55 D |
| 4,759,867 | A | | 7/1988 | Choy et al. ............. 252/143 |
| 4,861,511 | A | | 8/1989 | Kaplan .............. 252/174.23 |
| 4,874,537 | A | * | 10/1989 | Peterson et al. ............ 510/304 |
| 4,891,148 | A | | 1/1990 | Ouhadi et al. ............. 252/99 |
| 5,008,030 | A | | 4/1991 | Cook et al. ............. 252/106 |
| 5,039,441 | A | | 8/1991 | Thomas et al. ........... 252/142 |
| 5,061,393 | A | | 10/1991 | Linares et al. ........... 252/143 |
| 5,192,460 | A | | 3/1993 | Thomas et al. | |
| 5,205,957 | A | * | 4/1993 | Van de Pas ............. 510/397 |
| 5,256,328 | A | | 10/1993 | Cavanagh et al. ......... 252/102 |
| 5,368,767 | A | * | 11/1994 | Donker et al. ............ 510/369 |
| 5,445,756 | A | * | 8/1995 | Didier et al. ............ 510/303 |
| 5,562,850 | A | | 10/1996 | Woo et al. ............. 510/151 |
| 5,597,790 | A | * | 1/1997 | Thoen ................. 510/303 |
| 5,601,749 | A | * | 2/1997 | Hall et al. ............. 510/336 |
| 5,648,328 | A | | 7/1997 | Angell et al. ............ 510/441 |
| 5,814,592 | A | * | 9/1998 | Kahn et al. ............. 510/304 |
| 5,872,088 | A | * | 2/1999 | Pucci et al. ............. 510/238 |
| 5,872,092 | A | * | 2/1999 | Kong-Chan et al. ........ 510/413 |
| 5,945,490 | A | | 8/1999 | Veltman et al. .......... 510/191 |
| 5,990,061 | A | | 11/1999 | Veltman et al. .......... 510/191 |
| 6,001,789 | A | | 12/1999 | Trinh et al. ............ 510/191 |
| 6,008,172 | A | | 12/1999 | Broshi et al. ........... 510/135 |
| 6,037,316 | A | * | 3/2000 | Garner et al. ............ 510/238 |
| 6,083,890 | A | | 7/2000 | Miskiel et al. ........... 510/108 |
| 6,197,738 | B1 | | 3/2001 | Regutti ................. 510/383 |
| 6,235,127 | B1 | | 5/2001 | Rader et al. ............. 134/42 |
| 6,291,413 | B1 | * | 9/2001 | Miracle et al. ............ 510/313 |
| 6,294,186 | B1 | * | 9/2001 | Beerse et al. ............ 424/405 |
| 6,339,058 | B1 | | 1/2002 | Toussaint et al. | |
| 6,380,150 | B1 | | 4/2002 | Toussaint et al. | |
| 6,440,915 | B2 | | 8/2002 | Rader et al. ............. 510/191 |
| 6,467,699 | B1 | | 10/2002 | Vorlop et al. ............ 239/1 |
| 6,479,446 | B1 | * | 11/2002 | Sherry et al. ............ 510/238 |
| 6,627,590 | B1 | * | 9/2003 | Sherry et al. ............ 510/238 |
| 6,635,702 | B1 | * | 10/2003 | Schmucker-Castner et al. ............ 524/291 |
| 6,734,155 | B1 | * | 5/2004 | Herbots et al. ........... 510/392 |
| 6,767,880 | B1 | | 7/2004 | Foley et al. ............. 510/419 |
| 6,855,681 | B1 | | 2/2005 | Ness et al. ............. 510/349 |
| 2002/0183216 | A1 | | 12/2002 | Koening et al. .......... 510/130 |
| 2003/0092595 | A1 | | 5/2003 | Romero et al. ........... 510/447 |
| 2004/0018950 | A1 | | 1/2004 | Foley et al. ............. 510/218 |
| 2004/0033912 | A1 | | 2/2004 | Sakurai et al. ........... 510/101 |
| 2004/0171508 | A1 | | 9/2004 | Fregonese .............. 510/375 |

(Continued)

FOREIGN PATENT DOCUMENTS

EP 0216416 A2 4/1987

(Continued)

OTHER PUBLICATIONS

PCT International Search Report for PCT/GB02/03407 dated Oct. 14, 2002.

(Continued)

*Primary Examiner*—Charles Boyer
(74) *Attorney, Agent, or Firm*—Norris McLaughlin & Marcus PA

(57) ABSTRACT

The present invention is directed to a pourable acidic hard surface cleaning and/or disinfecting composition which contains suspended inclusions which appear as visibly discernible, discrete particulate materials, preferably where said discrete particulate materials are based on alginates.

21 Claims, No Drawings

U.S. PATENT DOCUMENTS

| | | | |
|---|---|---|---|
| 2004/0186037 A1 | 9/2004 | Cheung et al. | 510/426 |
| 2005/0020471 A1 | 1/2005 | Cheung et al. | 510/463 |
| 2005/0026801 A1 | 2/2005 | Broeckx et al. | 510/276 |
| 2005/0026802 A1 | 2/2005 | Kilkenny et al. | 510/295 |
| 2005/0043200 A1 | 2/2005 | Barry et al. | 510/421 |

FOREIGN PATENT DOCUMENTS

| | | |
|---|---|---|
| EP | 0240481 A1 | 10/1987 |
| EP | 0292910 A2 | 11/1988 |
| EP | 0919610 A1 | 10/1997 |
| EP | 0957156 | 5/1998 |
| EP | 1 010 751 A | 6/2000 |
| GB | 763547 | 11/1953 |
| GB | 2 066 660 | 12/1980 |
| GB | 2179055 A | 2/1987 |
| GB | 2288186 A | 10/1995 |
| GB | 2341870 | 3/2000 |
| WO | WO 97/02125 | 1/1997 |
| WO | WO 97/15649 | 5/1997 |
| WO | WO 99/35227 | 7/1999 |
| WO | WO 00/17303 | 3/2000 |
| WO | WO 01/00765 A1 | 1/2001 |
| WO | WO 01/57174 A1 | 8/2001 |
| WO | WO 01/77278 A | 10/2001 |
| WO | WO 03/020863 A | 3/2003 |

OTHER PUBLICATIONS

GB Search Report for GB 0211111.9 dated Feb. 20, 2002.
International Preliminary Report on Patentability dated Aug. 26, 2005 for application PCT/GB2004/000589.
Written Opinion of the International Searching Authority for application PCT/GB2004/000589.

* cited by examiner

HARD SURFACE CLEANER COMPRISING A SUSPENSION OF ALGINATE BEADS

The present application is a continuation in part application filed under 35 USC 111(a) of International Applications PCT/GB02/03407 filed Jul. 25, 2002 and PCT/GB04/000589 filed Feb. 17, 2004.

The present invention relates to pourable disinfecting hard surface cleaning compositions. More particularly the present invention relates to thickened lavatory cleaning compositions which provide a cleaning and disinfecting effect to hard surfaces, and which include visibly discernible inclusions.

Cleaning compositions which also provide a disinfecting or sanitizing effect are commercially important products. Such compositions enjoy a wide field of utility in assisting in the removal of stains and grime from surfaces, especially those characterized as useful with "hard surfaces". Hard surfaces are those which are frequently encountered in lavatories such as lavatory fixtures such as toilets, shower stalls, bathtubs, bidets, sinks, etc., as well as countertops, walls, floors, etc. Two types of commonly encountered stains in lavatories include "hard water" stains and "soap scum" stains. Such hard surfaces, and such stains, may also be found in different environments as well, including kitchens, hospitals, etc.

Various formulations in compositions of cleaning agents have been produced and are known to the art which cleaning agents are generally suited for one type of stain but not necessarily for both classes of stains. For example, it is known to the art that highly acidic cleaning agents comprising strong acids, such as hydrochloric acids, are useful in the removal of hard water stains. However, the presence of strong acids is known to be an irritant to the skin and further offers the potential of toxicological danger. Other classes of cleaning compositions and formulations are known to be useful upon soap scum stains, however, generally such compositions comprise an organic and/or inorganic acid, one or more synthetic detergents from commonly recognized classes such as those described in U.S. Pat. No. 5,061,393; U.S. Pat. No. 5,008,030; U.S. Pat. No. 4,759,867; U.S. Pat. No. 5,192,460; U.S. Pat. No. 5,039,441. Generally, the compositions described in these patents are claimed to be effective in the removal of soap scum stains from such hard surfaces and may find further limited use in other classes of stains.

However, the formulations of most of the compositions within the aforementioned patents generally have relatively high amounts of acids (organic and/or inorganic) which raises toxicological concerns, and further none of the above patents provide any disinfecting properties.

While many disinfecting hard surface cleaning compositions are known to the art, there is nonetheless a need for further improved compositions in the art.

According to the one aspect of the invention, there is provided a liquid pourable hard surface cleaning and/or disinfecting composition which comprises (preferably consists essentially of):

an acid constituent;
at least one nonionic surfactant;
suspended inclusions which appear as visibly discernible, discrete particulate materials, preferably where said discrete particulate materials are based on alginates; a thickener constituent;
optionally, at least one further detersive surfactant selected from anionic, amphoteric and zwitterionic surfactants;
optionally, but desirably at least one organic solvent;
optionally, one or more constituents for improving the aesthetic or functional features of the inventive compositions; and;
water.

Particularly preferred compositions according to the invention are acidic in character, are effective in the removal of both soap scum stains and hard water stains, and which compositions provide an effective sanitizing effect to hard surfaces.

In further aspects of the invention there are provided processes for the production of the aforesaid compositions.

It is yet a further object of the invention to provide a liquid pourable cleaning composition which features the benefits described above.

It is a further object of the invention to provide a process for the simultaneous cleaning and sanitization of hard surfaces, which process comprises the step of providing a composition as outlined above, and applying an effective amount to a hard surface requiring such treatment.

The present inventive compositions necessarily comprise an acid constituent which be a water soluble inorganic acid, or a water soluble organic acids. By way of non-limiting example useful inorganic acids include hydrochloric acid, phosphoric acid, sulfuric acid. With respect to water soluble organic acids, generally include at least one carbon atom, and include at least one carboxyl group (—COOH) in its structure. Preferred are water soluble organic acids which contain from 1 to about 6 carbon atoms, and at least one carboxyl group as noted. Particularly preferred amongst such organic acids are: formic acid, citric acid, sorbic acid, acetic acid, boric acid, maleic acid, adipic acid, lactic acid, malic acid, malonic acid, glycolic acid, and mixtures thereof. According to certain preferred embodiments however, the acid constituent is a combination of citric acid in combination with at least one further acid selected from the group consisting of sorbic acid, acetic acid, boric acid, formic acid, maleic acid, adipic acid, lactic acid, formic acid, malic acid, malonic acid, and glycolic acid. Most preferably, the acid constituent is a combination of citric acid with lactic acid, glycolic acid or malic acid.

As the inventive compositions are necessarily acidic in nature (pH<7.0) there should be sufficient acid present in the composition such that the pH of the composition is desirably less than 6, preferably from about 5.0 to about 1.0, more preferably from about 4.0 to about 1.0, and even more preferably from about 3.0 to about 1.0. Of course mixtures of two or more acids may be used, and the acid constituent may be present in any effective amount to provide a desired pH. Desirably however, the acid constituents is present in an amount not in excess of 20% wt. based on the total weight of the compositions; preferably the acid constituent is present in an amount of from about 0.05–20% wt., more preferably from about 0.5–20% wt., and most preferably is present in an amount of from about 1% wt. to about 15% wt.

The acid constituent of the inventive formulations provide free acidity within the cleaning composition, which free acid reacts with the fatty acid metal salts which are comprised within soap scum stains releasing the metal ions and freeing the fatty acid, which facilitates the removal of these undesired stains from hard surfaces. These acids also sequester the resulting free metal ions which are released from the soap scum stains. Also where the acids are selected to feature disinfecting properties, they concomitantly provide antimicrobial activity necessary to disinfect the cleaned surface.

The compositions of the present invention necessarily includes at least one anionic surfactant. Generally any anionic surfactant material may be used in the inventive compositions as this necessary constituent. By way of non-limiting example, particularly suitable anionic surfactants include: alkali metal salts, ammonium salts, amine salts, or aminoalcohol salts of one or more of the following compounds (linear and secondary): alcohol sulfates and sulfonates, alcohol phosphates and phosphonates, alkyl sulfates, alkyl ether sulfates, sulfate esters of an alkylphenoxy polyoxyethylene ethanol, alkyl monoglyceride sulfates, alkyl sulfonates, olefin sulfonates, paraffin sulfonates, beta-alkoxy alkane sulfonates, alkylamidoether sulfates, alkylaryl polyether sulfates, monoglyceride sulfates, alkyl ether sulfonates, ethoxylated alkyl sulfonates, alkylaryl sulfonates, alkyl benzene sulfonates, alkylamide sulfonates, alkyl monoglyceride sulfonates; alkyl carboxylates, alkyl sulfoacetates, alkyl ether carboxylates, alkyl alkoxy carboxylates having 1 to 5 moles of ethylene oxide, alkyl sulfosuccinates, alkyl ether sulfosuccinates, alkylamide sulfosuccinates, alkyl sulfosuccinamates, octoxynol or nonoxynol phosphates, alkyl phosphates, alkyl ether phosphates, taurates, N-acyl taurates, fatty taurides, fatty acid amide polyoxyethylene sulfates, isethionates, acyl isethionates, and sarcosinates, acyl sarcosinates, or mixtures thereof Generally, the alkyl or acyl radical in these various compounds comprise a carbon chain containing 12 to 20 carbon atoms.

Preferred anionic surfactants useful in forming the compositions of the invention include alkyl sulfates which may be represented by the following general formula:

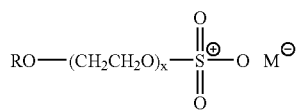

wherein R is an straight chain or branched alkyl chain having from about 8 to about 18 carbon atoms, saturated or unsaturated, and the longest linear portion of the alkyl chain is 15 carbon atoms or less on the average, M is a cation which makes the compound water soluble especially an alkali metal such as sodium, or is ammonium or substituted ammonium cation, and x is from 0 to about 4. Of these, most preferred are the non-ethoxylated $C_{12}$–$C_{15}$ primary and secondary alkyl sulfates.

Exemplary commercially available alkyl sulfates include one or more of those available under the tradenames RHODAPON® (ex. Rhône-Poulenc Co.) as well as STEPANOL® (ex. Stepan Chemical Co.). Exemplary alkyl sulfates which is preferred for use is a sodium lauryl sulfate surfactant presently commercially available as RHODAPON® LCP (ex. Rhône-Poulenc Co.), as well as a further sodium lauryl sulfate surfactant composition which is presently commercially available as STEPANOL® WAC (ex. Stepan Chemical Co.).

Further preferred anionic surfactants useful in forming the compositions of the invention include alkyl sulfonate anionic surfactants which may be represented according to the following general formula:

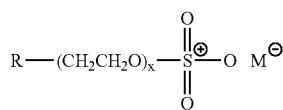

wherein R is an straight chain or branched alkyl chain having from about 8 to about 18 carbon atoms, saturated or unsaturated, and the longest linear portion of the alkyl chain is 15 carbon atoms or less on the average, M is a cation which makes the compound water soluble especially an alkali metal such as sodium, or is ammonium or substituted ammonium cation, and x is from 0 to about 4. Most preferred are the $C_{12}$–$C_{15}$ primary and secondary alkyl sulfates.

Exemplary, commercially available alkane sulfonate surfactants include one or more of those available under the tradename HOSTAPUR® (ex. Clariant). An exemplary and particularly alkane sulfonate which is preferred for use is a secondary sodium alkane sulfonate surfactant presently commercially available as HOSTAPUR® SAS from Hoechst Celanese.

The anionic surfactant is present in the compositions of the present invention in an amount of from about 0.01 to about 20% by weight, more preferably is present in an amount of from about 0.1–20% wt., and most preferably is present in an amount of from about 1% wt. to about 20% wt.

As a further necessary constituent, the inventive compositions comprise a thickener constituent. Thickeners useful in the present invention to achieve this viscosity are selected from the group consisting of cellulose, alkyl celluloses, alkoxy celluloses, hydroxy alkyl celluloses, alkyl hydroxy alkyl celluloses, carboxy alkyl celluloses, carboxy alkyl hydroxy alkyl celluloses, xanthan gum, gellan gum and mixtures thereof. Examples of the cellulose derivatives include ethyl cellulose, hydroxy ethyl cellulose, hydroxy propyl cellulose, carboxy methyl cellulose, carboxy methyl hydroxyethyl cellulose, hydroxypropyl cellulose, hydroxy propyl methyl cellulose, and ethyl hydroxy ethyl cellulose. Preferably, the thickener is a mixture of hydroxy ethyl cellulose and xanthan gum or is a mixture of xantham gum and gellan gum. Further specific preferred thickeners and combinations of thickeners are described in the Examples.

The amount of thickener present in the composition may be any amount which is effective in suspending the suspended inclusions as hereinafter described. Desirably the composition of the present of invention is thickened to a viscosity range of from about 100 to about 2000 centipoise, preferably to a viscosity of from about 750 to about 1500 centipoise, more preferably is in the range of about 800–1200 centipoise measured at room temperature, on a RVT Brookfield viscometer, spindle #2, at 60 rpm. Generally good thickening has been observed when the total amount of the thickeners are present in amount from about 0.1 to about 5% by weight, more preferably from about 0.1 to about 4% by weight, and most preferably from about 0.1% wt. to about 1% wt.

Preferably other thickening materials, particularly those based on synthetic polymers such as acrylic acid copolymers, e.g. Carbopol® materials, as well as those based on clays, and those based on cellulose including modified celluloses are desirably absent from the inventive compositions.

As a necessary constituent, the inventive compositions include suspended inclusions. These suspend inclusions appear as visibly discernible, discrete particulate materials to the consumer of the inventive compositions. These suspended inclusions desirably appear as small discrete visible particles suspended within the composition, particularly by a consumer having normal "20/20" vision. It is to be understood however that not all of the particulate materials present in the inventive composition need be visibly discernible as a portion of the particulate materials may be smaller than the visible threshold of the consumer having normal vision. It is nonetheless required that at least a substantial portion of the particulate materials present in the inventive composition need be visibly discernible as discrete particles.

Desirably the particulate materials are supplied to have an average particle size in the range of about 50 µm to about 1000 µm, preferably in the range of about 350 µm to about 1000 µm, most preferably in the range of about 450 µm to about 650 µm, and especially preferably in the range of about 575 µm to about 625 µm. Desirably the average particle size of these particulate materials represents that at least 85% of the particles, more preferably at least 90%, still more preferably at least 92%, and most preferably at least 90% of the particles present are within a specified range.

The suspended inclusions present in the inventive compositions are most desirably based on alginates although other visibly discernible, discrete particulate materials may be used as well, or in the place of alginate based materials. However the particularly preferred suspended inclusions are based on alginates.

Alginate based particulate materials used for the suspended inclusions in the inventive compositions may be formed from an alginate or salts of alginic acid such as potassium alginate, calcium alginate or sodium alginate salts, and advantageously may be conveniently harvested from naturally occurring seaweed especially of the species *Laminaria* wherein the sodium alginate form predominates. Alginates typically consist of sequences of α-L-guluronic acid and β-D-mannuronic acid which may be present in the alginate in various differing ratios. The term "beads" conveniently describes the geometry of the alginate based particulate materials as when these are formed form an aqueous slurry containing an alginate such as sodium alginate with one or more further constituents and then expelled to form individual particles or droplets, the coalescing aqueous slurry may form generally spherical particles, hence the term "beads". Of course, other processes for the formation of alginate based suspended inclusions are also contemplated as being useful in conjunction with the present invention such as processes wherein the alginate optionally containing one or more further constituents is comminuted by other methods, such as milling, grinding or other known art technique. In such instances the comminuted alginate based suspended inclusions may not necessarily form generally spherical particles but may form individual particles of irregular geometry. In such an instance the largest dimension of such individual particles of irregular geometry are used as the basis for determining the average particle size of the In a preferred embodiment the alginate beads are based on calcium alginates as the calcium salts of alginates are insoluble or poorly soluble in water, and thus are particularly desirable in the present inventive compositions which are substantially aqueous. The calcium salts of alginates used to form the alginate based particulate materials preferably exhibit little swelling or collapse when incorporated in the present inventive composition.

The alginate based particulate materials may contain from about 0.5% wt. to 100% wt. of an alginate or alginate salt, although quite frequently the amount of alginate in the alginate based particulate materials are much less, generally on from about 0.5% wt. to about 10% wt., more preferably from about 0.5% wt. to about 5% wt. Such alginate based particulate materials may be conveniently referred to as "alginate beads". Such alginate beads may be formed by a variety of known art processes including those described in the background section of PCT/US95/08313 to Thomas et al., as well as in U.S. Pat. No. 6,467,699 B1, the contents of which are incorporated by reference. Alternately such alginate based particulate materials may be commercially purchased from various suppliers, including geniaLab BioTechnologie (Braunschwig, Germany). As noted the composition of the alginate based particulate materials may include only a small proportion of an alginate or alginate salt, and may include one or more further non-alginate materials especially one or more inorganic materials such as titanium dioxide which improves the opacity, hence the visibility of the beads, as well as one or more coloring agents such as pigments such as ultramarine blue, said coloring agents which also improve the aesthetic appearance of the beads. Other further non-alginate materials not recited herein may also be include in the composition of the alginate based particulate materials. The alginate based particulate materials may be composed of a major proportion of water which is entrained within the structure of the discrete alginate based particulates and due to the highly porous character of alginates when in an aqueous compositions 80% wt., and usually 90% wt. or even greater of the mass of the discrete alginate based particulates may be water with the remaining balance to 100% wt. being the alginate or alginate salt, and one or more further non-alginate materials. Conveniently such alginate based particulate materials may be prepared, stored and sold as a slurry of discrete alginate based particulates in an aqueous-based carrier composition which may contain a minor amount of one or more further additives such as one or more salts especially chloride salts such as calcium chloride, as well as a preservative for inhibiting the growth of undesirable microorganisms in the slurry containing the discrete alginate based particulates. Preferred commercially available alginate based particulate material comprise from about 0.5% wt. to about 5% wt. of a calcium alginate, a pigment present in an amount up to about 0.01% wt., from about 0.1% wt. to about 5% wt. of TiO2 and the remaining balance of the mass of the alginate based particulate material comprised of a 2% calcium chloride solution in water which may also con an a minor amount, approx. 2% of calcium chloride. Such alginate based particulate material can be separated from the aqueous-based carrier composition by means of a fine sieve or other means for decanting the aqueous-based carrier composition from the alginate based particulate materials.

By the term "suspended" when referring to the inclusions, is to be understood that when the formed inventive compositions are manually shaken and then allowed to return to a quiescent state, such as by permitting them to stand on a tabletop or other surface at room temperature (approx. 20° C.) for 48 hours, the majority of the inclusions do not drop more than 7%, preferably do not drop more than 5%, most preferably do not drop more than 2% of their original distance as measured from the bottom of the container in which the inventive composition is present when they have returned to a quiescent state following manual shaking. By "majority of inclusions" is meant to convey that at least 90% of, preferably at least 95% and most preferably at least 97% of the inclusions physically present in the compositions. This is a particularly attractive and characteristic feature of preferred embodiments of inventive compositions, as the suspended inclusions do not appear to move perceptibly over long periods of time. Desirably, at least 90% of, preferably at least 95% and most preferably at least 97% of the inclusions physically present in the compositions do not drop more than 5%, most preferably do not drop more than 2% of their original distance from the bottom of the container in which the inventive composition is present when they have returned to a quiescent state following manual shaking when measured after 72 hours, more preferably when measured after 5 days, still more preferably when measured after 10 days, yet more preferably after 14 days when left in a quiescent state at room temperature. In certain particularly preferred embodiments of the invention at least 90% of, preferably at least 95% and most preferably at least 97% of the inclusions physically present in the compositions do not drop more than 5%, after 3 weeks and especially preferably after 4 weeks when retained in a quiescent state at room temperature.

Although optional, the compositions according to the present invention may include one or more further detersive surfactants particularly those selected from amongst further nonionic, amphoteric and zwitterionic surfactants, particularly those which may provide a detersive effect to the compositions.

Generally any nonionic surfactant material may be used in the inventive compositions. Practically any hydrophobic compound having a carboxy, hydroxy, amido, or amino group with a free hydrogen attached to the nitrogen can be condensed with an alkylene oxide, especially ethylene oxide or with the polyhydration product thereof, a polyalkylene glycol, especially polyethylene glycol, to form a water soluble or water dispersible nonionic surfactant compound. By way of non-limiting example, particularly examples of suitable nonionic surfactants which may be used in the present invention include the following:

One class of useful nonionic surfactants include polyalkylene oxide condensates of alkyl phenols. These compounds include the condensation products of alkyl phenols having an alkyl group containing from about 6 to 12 carbon atoms in either a straight chain or branched chain configuration with an alkylene oxide, especially an ethylene oxide, the ethylene oxide being present in an amount equal to 5 to 25 moles of ethylene oxide per mole of alkyl phenol. The alkyl substituent in such compounds can be derived, for example, from polymerized propylene, diisobutylene and the like. Examples of compounds of this type include nonyl phenol condensed with about 9.5 moles of ethylene oxide per mole of nonyl phenol; dodecylphenol condensed with about 12 moles of ethylene oxide per mole of phenol; dinonyl phenol condensed with about 15 moles of ethylene oxide per mole of phenol and diisooctyl phenol condensed with about 15 moles of ethylene oxide per mole of phenol.

A further class of useful nonionic surfactants include the condensation products of aliphatic alcohols with from about 1 to about 60 moles of an alkylene oxide, especially an ethylene oxide. The alkyl chain of the aliphatic alcohol can either be straight or branched, primary or secondary, and generally contains from about 8 to about 22 carbon atoms. Examples of such ethoxylated alcohols include the condensation product of myristyl alcohol condensed with about 10 moles of ethylene oxide per mole of alcohol and the condensation product of about 9 moles of ethylene oxide with coconut alcohol (a mixture of fatty alcohols with alkyl chains varying in length from about 10 to 14 carbon atoms). Other examples are those $C_6$–$C_{11}$ straight-chain alcohols which are ethoxylated with from about 3 to about 6 moles of ethylene oxide. Their derivation is well known in the art. Examples include Alfonic® 810-4.5, which is described in product literature from Sasol as a C8–10 having an average molecular weight of 356, an ethylene oxide content of about 4.85 moles (about 60 wt. %), and an HLB of about 12; Alfonic® 810-2, which is described in product literature as a $C_8$–$C_{10}$ having an average molecular weight of 242, an ethylene oxide content of about 2.1 moles (about 40 wt. %), and an HLB of about 12; and Alfonic® 610-3.5, which is described in product literature as having an average molecular weight of 276, an ethylene oxide content of about 3.1 moles (about 50 wt. %), and an HLB of 10. Other examples of alcohol ethoxylates are C10 oxo-alcohol ethoxylates available from BASF under the Lutensol® ON tradename. They are available in grades containing from about 3 to about 11 moles of ethylene oxide (available under the names Lutensol® ON 30; Lutensol® ON 50; Lutensol® ON 60; Lutensol® ON 65; Lutensol® ON 66; Lutensol® ON 70; Lutensol® ON 80; and Lutensol® ON 110). Other examples of ethoxylated alcohols include the Neodol® 91 series non-ionic surfactants available from Shell Chemical Company which are described as $C_9$–$C_{11}$ ethoxylated alcohols. The Neodol® 91 series non-ionic surfactants of interest include Neodol® 91-2.5, Neodol® 91-6, and Neodol® 91-8. Neodol® 91-2.5 has been described as having about 2.5 ethoxy groups per molecule, Neodol 91-6 has been described as having about 6 ethoxy groups per molecule; and Neodol 91-8 has been described as having about 8 ethoxy groups per molecule. Further examples of ethoxylated alcohols include the Rhodasurf® DA series non-ionic surfactants available from Rhodia which are described to be branched isodecyl alcohol ethoxylates. Rhodasurf® DA-530 has been described as having 4 moles of ethoxylation and an HLB of 10.5; Rhodasurf® DA-630 has been described as having 6 moles of ethoxylation with an HLB of 12.5; and Rhodasurf® DA-639 is a 90% solution of DA-630. Further examples of ethoxylated alcohols include those from Tomah Products (Milton, Wis.) under the Tomadol® tradename with the formula $RO(CH_2CH_2O)_nH$ where R is the primary linear alcohol and n is the total number of moles of ethylene oxide. The ethoxylated alcohol series from Tomah include 91-2.5; 91-6; 91-8—where R is linear $C_9/C_{10}/C_{11}$ and n is 2.5, 6, or 8; 1-3; 1-5; 1-7; 1-73B; 1-9; where R is linear $C_{11}$ and n is 3, 5, 7 or 9; 23-1; 23-3; 23-5; 23-6.5—where R is linear $C_{12}/C_{13}$ and n is 1, 3, 5, or 6.5; 25-3; 25-7, 25-9; 25-12—where R is linear $C_{12}/C_{13}/C_{14}/C_{15}$ and n is 3, 7, 9, or 12; and 45-7; 45-13—where R is linear $C_{14}/C_{15}$ and n is 7 or 13.

A further class of useful nonionic surfactants include primary and secondary linear and branched alcohol ethoxylates, such as those based on $C_6$–$C_{18}$ alcohols which further include an average of from 2 to 80 moles of ethoxylation per mol of alcohol. These examples include the Genapol® UD (ex. Clariant, Muttenz, Switzerland) described under the tradenames Genapol® UD 030, $C_{11}$-oxo-alcohol polyglycol ether with 3 EO; Genapol® UD, 050 $C_{11}$-oxo-alcohol polyglycol ether with 5 EO; Genapol® UD 070, $C_{11}$-oxo-alcohol polyglycol ether with 7 EO; Genapol® UD 080, $C_{11}$-oxo-alcohol polyglycol ether with 8 EO; Genapol® UD 088, $C_{11}$-oxo-alcohol polyglycol ether with 8 EO; and Genapol® UD 110, $C_{11}$-oxo-alcohol polyglycol ether with 11 EO.

A further class of useful nonionic surfactants includethose surfactants having a formula $RO(CH_2CH_2O)_nH$ wherein R is a mixture of linear, even carbon-number hydrocarbon chains ranging from $C_{12}H_{25}$ to $C_{16}H_{33}$ and n represents the number of repeating units and is a number of from about 1 to about 12. Surfactants of this formula are presently marketed under the Genapol® tradename (ex. Clariant), which surfactants include the "26-L" series of the general formula $RO(CH_2CH_2O)_nH$ wherein R is a mixture of linear, even carbon-number hydrocarbon chains ranging from $C_{12}H_{25}$ to $C_{16}H_{33}$ and n represents the number of repeating units and is a number of from 1 to about 12, such as 26-L-1, 26-L-1.6, 26-L-2, 26-L-3, 26-L-5, 26-L-45, 26-L-50, 26-L-60, 26-L-60N, 26-L-75, 26-L-80, 26-L-98N, and the 24-L series, derived from synthetic sources and typically contain about 55% $C_{12}$ and 45% $C_{14}$ alcohols, such as 24-L-3, 24-L-45, 24-L-50, 24-L-60, 24-L-60N, 24-L-75, 24-L-92, and 24-L-98N, all sold under the Genapol® tradename.

A further class of useful nonionic surfactants include alkoxy block copolymers, and in particular, compounds based on ethoxy/propoxy block copolymers. Polymeric alkylene oxide block copolymers include nonionic surfactants in which the major portion of the molecule is made up of block polymeric $C_2$–$C_4$ alkylene oxides. Such nonionic surfactants, while preferably built up from an alkylene oxide chain starting group, and can have as a starting nucleus almost any active hydrogen containing group including, without limitation, amides, phenols, thiols and secondary alcohols.

One group of such useful nonionic surfactants containing the characteristic alkylene oxide blocks are those which may be generally represented by the formula (A):

$$HO—(EO)_x(PO)_y(EO)_z—H \quad (A)$$

where
EO represents ethylene oxide,
PO represents propylene oxide,
y equals at least 15,
$(EO)_{x+y}$ equals 20 to 50% of the total weight of said compounds, and, the total molecular weight is preferably in the range of about 2000 to 15,000. These surfactants are available under the PLURONIC (ex. BASF) or Emulgen (ex. Kao.) A further group of such useful nonionic surfactants containing the characteristic alkylene oxide blocks are those can be represented by the formula (B):

$$R—(EO,PO)_a(EO,PO)_b—H \quad (B)$$

wherein R is an alkyl, aryl or aralkyl group, where the R group contains 1 to 20 carbon atoms, the weight percent of EO is within the range of 0 to 45% in one of the blocks a, b, and within the range of 60 to 100% in the other of the blocks a, b, and the total number of moles of combined EO and PO is in the range of 6 to 125 moles, with 1 to 50 moles in the PO rich block and 5 to 100 moles in the EO rich block. Specific nonionic surfactants which in general are encompassed by Formula B include butoxy derivatives of propylene oxide/ethylene oxide block polymers having molecular weights within the range of about 2000–5000.

Still further examples of useful nonionic surfactants include those which can be represented by formula (C) as follows:

$$RO—(BO)_n(EO)_x—H \quad (C)$$

wherein
EO represents ethylene oxide,
BO represents butylene oxide,
R is an alkyl group containing 1 to 20 carbon atoms,
n is about 5–15 and x is about 5–15.

Yet further useful nonionic surfactants include those which may be represented by the following formula (D):

$$HO—(EO)_x(BO)_n(EO)_y—H \quad (D)$$

wherein
EO represents ethylene oxide,
BO represents butylene oxide,
n is about 5–15, preferably about 15,
x is about 5–15, preferably about 15, and
y is about 5–15, preferably about 15.

Still further exemplary useful nonionic block copolymer surfactants include ethoxylated derivatives of propoxylated ethylene diamine, which may be represented by the following formula:

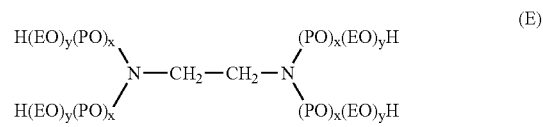

where
(EO) represents ethoxy,
(PO) represents propoxy, the amount of $(PO)_x$ is such as to provide a molecular weight prior to ethoxylation of about 300 to 7500, and the amount of $(EO)_y$ is such as to provide about 20% to 90% of the total weight of said compound.

Further useful non-ionic surfactants which may be used in the inventive compositions include those presently marketed under the trade name Pluronics® (ex. BASF). The compounds are formed by condensing ethylene oxide with a hydrophobic base formed by the condensation of propylene oxide with propylene glycol. The molecular weight of the hydrophobic portion of the molecule is of the order of 950 to 4,000 and preferably 200 to 2,500. The addition of polyoxyethylene radicals of the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants are in liquid form and particularly satisfactory surfactants are available as those marketed as Pluronics® L62 and Pluronics® L64.

Alkylmonoglyocosides and alkylpolyglycosides which find use in the present inventive compositions include known nonionic surfactants which are alkaline and electrolyte stable. Alkylmonoglyocosides and alkylpolyglycosides are prepared generally by reacting a monosaccharide, or a compound hydrolyzable to a monosaccharide with an alcohol such as a fatty alcohol in an acid medium. Various glycoside and polyglycoside compounds including alkoxylated glycosides and processes for making them are disclosed in U.S. Pat. Nos. 2,974,134; 3,219,656; 3,598,865; 3,640,998; 3,707,535, 3,772,269; 3,839,318; 3,974,138; 4,223,129 and 4,528,106 the contents of which are incorporated by reference.

One exemplary group of such useful alkylpolyglycosides include those according to the formula:

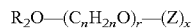

$$R_2O—(C_nH_{2n}O)_r—(Z)_x$$

wherein:
$R_2$ is a hydrophobic group selected from alkyl groups, alkylphenyl groups, hydroxyalkylphenyl groups as well as mixtures thereof, wherein the alkyl groups may be straight chained or branched, and which contain from about 8 to about 18 carbon atoms, n has a value of 2–8, especially a value of 2 or 3;
r is an integer from 0 to 10, but is preferably 0,
Z is derived from glucose; and,
x is a value from about 1 to 8, preferably from about 1.5 to 5. Preferably the alkylpolyglycosides are nonionic fatty alkylpolyglucosides which contain a straight chain or branched chain $C_8$–$C_{15}$ alkyl group, and have an average of from about 1 to 5 glucose units per fatty alkylpolyglucoside molecule. More preferably, the nonionic fatty alkylpolyglucosides which contain straight chain or branched $C_8-C_{15}$ alkyl group, and have an average of from about 1 to about 2 glucose units per fatty alkylpolyglucoside molecule.

A further exemplary group of alkyl glycoside surfactants suitable for use in the practice of this invention may be presented by the following formula (A):

$$RO-(R_1O)_y-(G)_x-Z_b \qquad (A)$$

wherein:
R is a monovalent organic radical containing from about 6 to about 30, preferably from about 8 to 18 carbon atoms,
$R_1$ is a divalent hydrocarbon radical containing from about 2 to about 4 carbon atoms,
y is a number which has an average value from about 0 to about 1 and is preferably 0,
G is a moiety derived from a reducing saccharide containing 5 or 6 carbon atoms; and,
x is a number having an average value from about 1 to 5 (preferably from 1.1 to 2);
Z is $O_2M^1$,

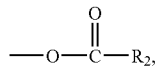

$O(CH_2)$, $CO_2M^1$, $OSO_3M^1$, or $O(CH_2)SO_3M^1$;
$R_2$ is $(CH_2)CO_2M^1$ or $CH=CHCO_2M^1$; (with the proviso that Z can be $O_2M^1$ only if Z is in place of a primary hydroxyl group in which the primary hydroxyl-bearing carbon atom, $-CH_2OH$, is oxidized to form a

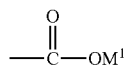

group)
b is a number of from 0 to 3x+1 preferably an average of from 0.5 to 2 per glycosal group;
p is 1 to 10,
$M^1$ is $H^+$ or an organic or inorganic counterion, particularly cations such as, for example, an alkali metal cation, ammonium cation, monoethanolamine cation or calcium cation. As defined in Formula (A) above, R is generally the residue of a fatty alcohol having from about 8 to 30 and preferably 8 to 18 carbon atoms. Examples of such alkylglycosides as described above include, for example APG 325 CS Glycoside® which is described as being a 50% $C_9-C_{11}$ alkyl polyglycoside, also commonly referred to as D-glucopyranoside, (commercially available from Henkel KGaA) and Glucopon® 625 CS which is described as being a 50% $C_{10}-C_{16}$ alkyl polyglycoside, also commonly referred to as a D-glucopyranoside, (ex. Henkel).

Further nonionic surfactants which may be included in the inventive compositions include alkoxylated alkanolamides, preferably C8–C24 alkyl di(C2–C3 alkanol amides), as represented by the following formula:

$$R_5-CO-NH-R_6-OH$$

wherein $R_5$ is a branched or straight chain $C_8-C_{24}$ alkyl radical, preferably a $C_{10}-C_{16}$ alkyl radical and more preferably a $C_{12}-C_{14}$ alkyl radical, and $R_6$ is a $C_1-C_4$ alkyl radical, preferably an ethyl radical.

The inventive compositions may also include a nonionic amine oxide constituent. Exemplary amine oxides include:
(A) Alkyl di (lower alkyl) amine oxides in which the alkyl group has about 10–20, and preferably 12–16 carbon atoms, and can be straight or branched chain, saturated or unsaturated. The lower alkyl groups include between 1 and 7 carbon atoms. Examples include lauryl dimethyl amine oxide, myristyl dimethyl amine oxide, and those in which the alkyl group is a mixture of different amine oxide, dimethyl cocoamine oxide, dimethyl (hydrogenated tallow) amine oxide, and myristyl/palmityl dimethyl amine oxide,
(B) Alkyl di (hydroxy lower alkyl) amine oxides in which the alkyl group has about 10–20, and preferably 12–16 carbon atoms, and can be straight or branched chain, saturated or unsaturated. Examples are bis(2-hydroxyethyl) cocoamine oxide, bis(2-hydroxyethyl) tallowamine oxide; and bis(2-hydroxyethyl) stearylamine oxide;
(C) Alkylamidopropyl di(lower alkyl) amine oxides in which the alkyl group has about 10–20, and preferably 12–16 carbon atoms, and can be straight or branched chain, saturated or unsaturated. Examples are cocoamidopropyl dimethyl amine oxide and tallowamidopropyl dimethyl amine oxide; and
(D) Alkylmorpholine oxides in which the alkyl group has about 10–20, and preferably 12–16 carbon atoms, and can be straight or branched chain, saturated or unsaturated.

Preferably the amine oxide constituent is an alkyl di (lower alkyl) amine oxide as denoted above and which may be represented by the following structure:

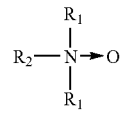

wherein each:
$R_1$ is a straight chained $C_1-C_4$ alkyl group, preferably both $R_1$ are methyl groups; and,
$R_2$ is a straight chained $C_8-C_{18}$ alkyl group, preferably is $C_{10}-C_{14}$ alkyl group, most preferably is a $C_{12}$ alkyl group.

Each of the alkyl groups may be linear or branched, but most preferably are linear. Most preferably the amine oxide constituent is lauryl dimethyl amine oxide. Technical grade mixtures of two or more amine oxides may be used, wherein amine oxides of varying chains of the $R_2$ group are present. Preferably, the amine oxides used in the present invention include $R_2$ groups which comprise at least 50% wt., preferably at least 60% wt. of $C_{12}$ alkyl groups and at least 25% wt. of $C_{14}$ alkyl groups, with not more than 15% wt. of $C_{16}$, $C_{18}$ or higher alkyl groups as the $R_2$ group.

Of course the nonionic surfactant constituent, when present, my comprise two or more nonionic surfactants. In certain preferred embodiments the inventive compositions comprise at least one nonionic surfactant. When present, any nonionic surfactants present in the compositions of the present invention are desirably included in an amount of from about 0.01% wt. to about 20% wt., more preferably, is present in an amount of from about 0.1–20% wt., and most preferably is present in an amount of from about 1 to about 10% wt.

The compositions according to the invention may optionally further comprise an alkyl ethoxylated carboxylate surfactant. In particular, the alkyl ethoxylated carboxylate comprises compounds and mixtures of compounds which may be represented by the formula:

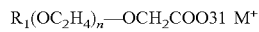

wherein $R_1$ is a $C_4$–$C_8$ alkyl, n is from about 3 to about 20, and M is hydrogen, a solubilizing metal, preferably an alkali metal such as sodium or potassium, or ammonium or lower alkanolammonium, such as triethanolammonium, monoethanolammoniuin, or diisopropanolammonium. The lower alkanol of such alkanolammonium will normally be of 2 to 4 carbon atoms and is preferably ethanol. Preferably, R1 is a $C_{12}$–$C_{15}$ alkyl, n is from about 7 to about 13, and M is an alkali metal counterion.

Examples of alkyl ethoxylated carboxylates contemplated to be useful in the present invention include, but are not necessarily limited to, sodium buteth-3 carboxylate, sodium hexeth-4 carboxylate, sodium laureth-5 carboxylate, sodium laureth-6 carboxylate, sodium laureth-8 carboxylate, sodium laureth-11 carboxylate, sodium laureth-13carboxylate, sodium trideceth-3 carboxylate, sodium trideceth-6 carboxylate, sodium trideceth-7 carboxylate, sodium trideceth-19 carboxylate, sodium capryleth-4 carboxylate, sodium capryleth-6 carboxylate, sodium capryleth-9 carboxylate, sodium capryleth-13carboxylate, sodium ceteth-13carboxylate, sodium $C_{12-15}$ pareth-6 carboxylate, sodium $C_{12-15}$ pareth-7 carboxylate, sodium $C_{14-15}$ pareth-8 carboxylate, isosteareth-6 carboxylate as well as the acid form. Sodium-laureth-8 carboxylate, sodium laureth-13carboxylate, pareth-25-7 carboxylic acid are preferred. A particularly preferred sodium laureth-13 carboxylate can be obtained from Clariant Corp. under the trade name Sandopan® LS-24.

When present, any alkyl ethoxylated carboxylate surfactant present in the compositions of the present invention are desirably included in an amount of from about 0.1 to about 20% by weight, more preferably is present in an amount of from about 0.1–20% wt., and most preferably is present in an amount of from about 1 to about 10% wt. By way of non-limiting example exemplary amphoteric surfactants include one or more water-soluble betaine surfactants which may be represented by the general formula:

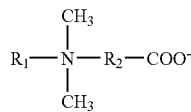

wherein $R_1$ is an alkyl group containing from 8 to 18 carbon atoms, or the amido radical which may be represented by the following general formula:

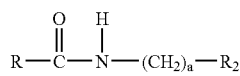

wherein R is an alkyl group having from 8 to 18 carbon atoms, a is an integer having a value of from 1 to 4 inclusive, and $R_2$ is a $C_1$–$C_4$ alkylene group. Examples of such water-soluble betaine surfactants include dodecyl dimethyl betaine, as well as cocoamidopropylbetaine.

When present, any amphoteric surfactants present in the compositions of the present invention are desirably included in an amount of from about 0.1 to about 20% by weight, more preferably is present in an amount of from about 0.1–20% wt., and most preferably is present in an amount of from about 1 to about 10% wt.

Most desirably, the total amount of detersive surfactants present in the inventive compositions, inclusive of the necessary anionic surfactants and any further optional surfactants does not exceed about 20% wt., more preferably does not exceed about 15% wt.

Optionally, but in many cases desirably, the inventive compositions comprise one or more organic solvents. By way of non-limiting example exemplary useful organic solvents which may be included in the inventive compositions include those which are at least partially water-miscible such as alcohols (e.g., low molecular weight alcohols, such as, for example, ethanol, propanol, isopropanol, and the like), glycols (such as, for example, ethylene glycol, propylene glycol, hexylene glycol, and the like), water-miscible ethers (e.g. diethylene glycol diethylether, diethylene glycol dimethylether, propylene glycol dimethylether), water-miscible glycol ether (e.g. propylene glycol monomethylether, propylene glycol mono ethylether, propylene glycol mono-propylether, propylene glycol monobutylether, ethylene glycol monobutylether, dipropylene glycol monomethylether, diethyleneglycol monobutylether), lower esters of monoalkylethers of ethylene glycol or propylene glycol (e.g. propylene glycol monomethyl ether acetate), and mixtures thereof. Glycol ethers having the general structure $R_a$—$R_b$—OH, wherein $R_a$ is an alkoxy of 1 to 20 carbon atoms, or aryloxy of at least 6 carbon atoms, and $R_b$ is an ether condensate of propylene glycol and/or ethylene glycol having from one to ten glycol monomer units. Of course, mixtures of two or more organic solvents may be used in the organic solvent constituent.

When present, the organic solvent constituent may be present in amounts of from about 0.1 to about 20% by weight, more preferably is present in an amount of from about 0.1–10% wt., and most preferably is present in an amount of from about 1 to about 10% wt.

According to certain particularly preferred embodiments, the inventive compositions exclude added organic solvents, particularly those described immediately above. While it is recognized that organic solvents may be present as carriers for certain other constituents essential to the present invention, and these may be present; generally the total amount of such organic solvents included in constituents provided from supplies, if present, is less than about than 0.1% wt., more preferably less than 0.05% wt. and most preferably comprise no organic solvents as described above. According to such certain particularly preferred embodiments, the inventive compositions include no organic solvents which are added other than those which may or may not be present in one or more of the constituents from the supplier thereof. According to especially particularly preferred embodiments, the inventive compositions include no organic solvents.

While optional, the compositions of the invention may further include an oxidizing agent, which is preferably a peroxyhydrate or other agent which releases hydrogen peroxide in aqueous solution. Such materials are per se, known to the art. Such peroxyhydrates are to be understood as to encompass hydrogen peroxide as well as any material or compound which in an aqueous composition yields hydrogen peroxide. Examples of such materials and compounds include without limitation: alkali metal peroxides including sodium peroxide and potassium peroxide, alkali perborate monohydrates, alkali metal perborate tetrahydrates, alkali metal persulfate, alkali metal percarbonates, alkali metal peroxyhydrate, alkali metal peroxydihydrates, and alkali metal carbonates especially where such alkali metals are sodium or potassium. Further useful are various peroxydihydrate, and organic peroxyhydrates such as urea peroxide. Desirably the oxidizing agent is hydrogen peroxide.

Desirably the oxidizing agent, especially the preferred hydrogen peroxide is present in the inventive compositions in an amount of from about 0.01% wt. to about 10.0% wt., based on the total weight of the composition of which it forms a part.

Minor amounts of stabilizers such as one or more organic phosphonates, stannates, pyrophosphates, as well as citric acid as well as citric acid salts may be included and are considered as part of the oxidizing agent. The inclusion of one or more such stabilizers aids in reducing the decomposition of the hydrogen peroxide due to the presence of metal ions and or adverse pH levels in the inventive compositions.

The compositions of the present invention can also optionally comprise one or more further constituents which are directed to improving the aesthetic or functional features of the inventive compositions. By way of non-limiting example such further constituents include one or more coloring agents, fragrances and fragrance solubilizers, viscosity modifying agents, other surfactants, pH adjusting agents and pH buffers including organic and inorganic salts, optical brighteners, opacifying agents, hydrotropes, anti-foaming agents, enzymes, anti-spotting agents, anti-oxidants, preservatives, and anti-corrosion agents. When one or more of the optional constituents is added, i.e., fragrance and/or coloring agents, the esthetic and consumer appeal of the product is often favorably improved. The use and selection of these optional constituents is well known to those of ordinary skill in the art. When present, the one or more optional constituents present in the inventive compositions do not exceed about 20% wt., preferably do not exceed 15% wt., and most preferably do not exceed 10% wt.

Certain optional constituents which are nonetheless desirably present in the inventive compositions are pH adjusting agents and especially pH buffers. Such pH buffers include many materials which are known to the art and which are conventionally used in hard surface cleaning and/or hard surface disinfecting compositions. By way of non-limiting example pH adjusting agents include phosphorus containing compounds, monovalent and polyvalent salts such as of silicates, carbonates, and borates, certain acids and bases, tartrates and certain acetates. Further exemplary pH adjusting agents include mineral acids, basic compositions, and organic acids, which are typically required in only minor amounts. By way of further non-limiting example pH buffering compositions include the alkali metal phosphates, polyphosphates, pyrophosphates, triphosphates, tetraphosphates, silicates, metasilicates, polysilicates, carbonates, hydroxides, and mixtures of the same. Certain salts, such as the alkaline earth phosphates, carbonates, hydroxides, can also function as buffers. It may also be suitable to use as buffers such materials as aluminosilicates (zeolites), borates, aluminates and certain organic materials such as gluconates, succinates, maleates, and their alkali metal salts. When present, the pH adjusting agent, especially the pH buffers are present in an amount effective in order to maintain the pH of the inventive composition within a target pH range.

As the compositions are largely aqueous in nature, and comprises as the balance of the composition water in to order to provide to 100% by weight of the compositions of the invention. The water may be tap water, but is preferably distilled and is most preferably deionized water. If the water is tap water, it is preferably substantially free of any undesirable impurities such as organics or inorganics, especially mineral salts which are present in hard water which may thus undesirably interfere with the operation of the constituents present in the aqueous compositions according to the invention.

The inventive compositions provide certain technical benefits when used on hard surfaces, particularly: satisfactory removal of hard water stains, satisfactory removal of soap scum stains, and satisfactory disinfection or sanitization of hard surfaces. In preferred embodiments, the compositions are readily pourable and are be desirably provided as a ready to use pourable product in a manually squeezable (manually deformable) bottle. In use, the consumer generally applies an effective amount of the composition and within a few moments thereafter, wipes off the treated area with a rag, towel, brush or sponge, usually a disposable paper towel or sponge. In certain applications, however, especially where undesirable stain deposits are heavy, the composition according to the invention may be left on the stained area until it has effectively loosened the stain deposits after which it may then be wiped off, rinsed off, or otherwise removed. For particularly heavy deposits of such undesired stains, multiple applications may also be used.

A particularly advantageous feature of the inventive compositions is that as the suspended inclusions are visibly discrete and visibly discernible to the consumer, these same inclusions are visible to the consumer on hard surfaces to which the inventive compositions have been applied. This permits for ready visual inspection of the coverage of the hard surface by an inventive composition immediately after application of the composition by a consumer. Such provides not only an attractive attribute to commercial products based on such compositions but also provides a visual indicator to the consumer of thorough coverage and contact with hard surfaces. This visual indicator provides an important means whereby the consumer may visually inspect a surface, particularly a surface wherein the presence of undesired microorganisms is suspected, to ensure that thorough coverage and contact with said hard surface is realized. As is known, physical contact between the inventive composition and undesired microorganisms is required in order to the inventive compositions to provide a disinfecting effect.

An important technical characteristic lies in rheology of the inventive compositions. The compositions may be described as being rheopectic at lower shear rates, an especially upon standing in quiescent state, but are thixotropic at higher shear rates. Such dual properties are very advantageous, as when the compositions are at rest in a container, e.g., upon standing, their rheopectic behavior provides for the stable suspension of the inclusions described herein. When it is desired to dispense the compositions from a container especially through the nozzle of a bottle, the thixotropic characteristics of the compositions permit for their dispensing through the nozzle of such a bottle. Ideally, after being dispensed from such a squeezable bottle onto a surface, especially an inclined surface the compositions return to a quiescent state and once again display a rheopectic behavior. Furthermore, as at least some of the suspended inclusions are delivered from the composition and onto the surface, these inclusions are present on the surface and provide a useful indicator as to the coverage of the dispensed composition onto the surface. Preferably the inventive compositions are provided in a non-pressurized squeeze bottle package which provides for the dispensing of the compositions through a nozzle, but not through a trigger spray, other pump mechanism or via an aerosol nozzle.

The inventive compositions are desirably provided as a ready to use product which may be directly applied to a hard surface. By way of example, hard surfaces suitable for coating with the polymer include surfaces composed of refractory materials such as: glazed and unglazed tile, brick, porcelain, ceramics as well as stone including marble, granite, and other stones surfaces; glass; metals; plastics e.g. polyester, vinyl; fiberglass, Formica®, Corian® and other hard surfaces known to the industry. Hard surfaces which are to be particularly denoted are lavatory fixtures such as shower stalls, bathtubs and bathing appliances (racks, curtains, shower doors, shower bars) toilets, bidets, wall and flooring surfaces especially those which include refractory materials and the like. Further hard surfaces which are to be denoted are those associated with kitchen environments and other environments associated with food preparation, including cabinets and countertop surfaces as well as walls and floor surfaces especially those which include refractory materials, plastics, Formica®, Corian® and stone. Still further hard surfaces include those associated with medical facilities, e.g., hospitals, clinics as well as laboratories, e.g., medical testing laboratories.

The compositions according to the invention are easily produced by any of a number of known art techniques. Conveniently, a part of the water is supplied to a suitable mixing vessel further provided with a stirrer or agitator, and while stirring, the remaining constituents are added to the mixing vessel, including any final amount of water needed to provide to 100% wt. of the inventive composition.

The following examples below illustrate exemplary formulations and preferred formulations of the inventive composition. It is to be understood that these examples are presented by means of illustration only and that further useful formulations fall within the scope of this invention and the claims may be readily produced by one skilled in the art and not deviate from the scope and spirit of the invention. Throughout this specification and in the accompanying claims, weight percents of any constituent are to be understood as the weight percent of the active portion of the referenced constituent, unless otherwise indicated.

EXAMPLES

Exemplary formulations illustrating certain preferred embodiments of the inventive compositions and described in more detail in Table 1 below were formulated generally in accordance with the following protocol.

Into a suitably sized vessel, a measured amount of water was provided after which the constituents were added in the following sequence: thickening agents, surfactant(s), acid and then the remaining constituents. Mixing, which generally lasted from 5 minutes to 120 minutes was maintained until the particular formulation appeared to be homogeneous. The exemplary compositions were readily pourable, and retained well mixed characteristics (i.e., stable mixtures) upon standing. The constituents may be added in any order.

Examples of inventive formulations are shown in Table 1 below (the indicated constituents are provided as "100% active") wherein the amounts of each named constituents are indicated in % w/w. Deionized water was added in "quantum sufficient" to provide the balance to 100 parts by weight of the compositions.

TABLE 1

|  | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
| --- | --- | --- | --- | --- | --- | --- | --- | --- | --- | --- | --- | --- |
| hydroxyethylcellulose | 0.1 | 0.1 | 0.1 | 0.1 | 0.1 | 0.1 | 0.1 | 0.1 | 0.1 | 0.1 | 0.1 | — |
| xanthan gum | 0.4 | 0.4 | 0.4 | 0.4 | 0.4 | 0.4 | 0.4 | 0.4 | 0.4 | 0.4 | 0.4 | 0.2 |
| gellan gum | — | — | — | — | — | — | — | — | — | — | — | 0.05 |
| sodium lauryl sulfate | 2.0 | 2.0 | 2.0 | 2.0 | 2.0 | 2.0 | 2.0 | 2.0 | 2.0 | 2.0 | 2.0 | 2.0 |
| citric acid | 4.0 | 2.0 | 2.0 | 2.0 | 2.0 | 2.0 | 2.0 | 2.0 | 2.0 | 2.0 | 2.0 | 2.0 |
| formic acid | — | 2.0 | — | — | — | — | — | — | — | — | — | — |
| malonic acid | — | — | — | — | 2.0 | — | — | — | — | — | — | — |
| maleic acid | — | — | — | — | — | 2.0 | — | — | — | — | — | — |
| adipic acid | — | — | 2.0 | — | — | — | — | — | — | — | — | — |
| boric acid | — | — | — | 2.0 | — | — | — | — | — | — | — | — |
| lactic acid | — | — | — | — | — | — | — | — | — | 2.3 | — | 2.0 |
| glycolic acid | — | — | — | — | — | — | — | — | — | — | 2.0 | — |
| malic acid | — | — | — | — | — | — | 2.0 | — | — | — | — | — |
| acetic acid | — | — | — | — | — | — | — | 2.0 | — | — | — | — |
| sorbic acid | — | — | — | — | — | — | — | — | 2.0 | — | — | — |
| sodium hydroxide | 0.5 | 0.77 | 0.34 | 0.34 | 0.34 | 0.34 | 0.34 | 0.34 | 0.34 | 0.28 | 0.34 | 0.34 |
| dye | 1 | 1 | 1 | 1 | 1 | 1 | 1 | 1 | 1 | 1 | 1 | — |
| fragrance | 0.28 | 0.28 | 0.28 | 0.28 | 0.28 | 0.28 | 0.28 | 0.28 | 0.28 | 0.28 | 0.28 | 0.21 |
| alginate beads | 0.5 | 0.5 | 0.5 | 0.5 | 0.5 | 0.5 | 0.5 | 0.5 | 0.5 | 0.5 | 0.5 | 0.3 |
| pH | 2.92 | 2.92 | 2.99 | 2.94 | 3.01 | 3.01 | 3.0 | 2.95 | 2.98 | 2.88 | 2.96 | — |
| di water | q.s. | q.s. | q.s. | q.s. | q.s. | q.s. | q.s. | q.s. | q.s. | q.s. | q.s. | q.s. |

The identity of the individual constituents indicated above is listed on the following table wherein is indicated the generic name, the commercial preparation used, the percent active weight (% w/w basis) of the compound identified by the generic name, and in some cases the supplier of the commercial preparation:

TABLE 2

| | |
| --- | --- |
| hydroxyethylcellulose | CELLOSIZE QP-100MH (100%) (ex. Union Carbide, division of Dow Chemical) |
| xanthan gum | KELZAN ASXT (100%) (ex. Kelco) |
| gellan gum | KELCOGEL AFT (100%) (ex. Kelco) |
| sodium lauryl sulfate | Stepanol WAC (30%) (ex. Stepan Co.), except for Ex. 12 where Stepanol LCP (30%) a low cloud point sodium lauryl sulfate was used |
| citric acid | anhydrous citric acid (100%) (ex. ADM) |
| formic acid | formic acid (94%) |
| malonic acid | malonic acid (99%) |
| maleic acid | maleic acid (100%) |
| adipic acid | adipic acid (98%) |

TABLE 2-continued

| | |
|---|---|
| boric acid | boric acid (99.5%) |
| lactic acid | lactic acid (88%) |
| glycolic acid | glycolic acid (70%) (ex. DuPont) |
| malic acid | malic acid (100%) |
| acetic acid | acetic acid (100%) |
| sorbic acid | sorbic acid (100%) |
| sodium hydroxide | NaOH pellets, anhydrous (100%) |
| dye | 1% aqueous solution of a FD&C yellow dye |
| fragrance | proprietary composition |
| alginate beads | alginate based particulate material compsiring less than 5% wt of calcium alginate, less than 0.01% wt. of a pigment, less than 5% wt. of TiO$_2$ and the balance to 100% wt. water drained from an aqueous carrier containing 2% calcium chloride in solution (ex. geniaLabs Biotechnologie, Germany) |
| di water | deionized water |

Certain of the compositions described on Table 1 above were tested to evaluate certain technical characteristics of the compositions.

Evaluation of Composition Stability:

Certain of the compositions described on Table 1 were evaluated to observe the stability of the alginate beads in the compositions following storage of the compositions under accelerated ageing testing, wherein the compositions were stored for 1 week at 49° C. The results are indicated in the following Table:

TABLE 3

| | |
|---|---|
| Ex. 1 | stable |
| Ex. 2 | stable |
| Ex. 3 | swell |
| Ex. 4 | swell |
| Ex. 5 | swell |
| Ex. 6 | swell |
| Ex. 7 | stable |
| Ex. 8 | swell |
| Ex. 9 | swell |
| Ex. 10 | stable |
| Ex. 11 | stable |

A result of "stable" indicated that the suspended inclusions based on the alginate based particulate materials did not change in from their initial appearance at the conclusion of the test. A result of "swell" indicated that the suspended inclusions based on the alginate based particulate materials slightly to somewhat changed in from their initial appearance at the conclusion of the test. In all of the formulations however the alginate based particulate materials were stably suspended inclusions.

All of the compositions of Table 1, after being manually shaken and then allowed to return to a quiescent state by permitting them to stand on a laboratory bench tabletop at room temperature (approx. 20° C.) for 48 hours, exhibited the behavior that the majority of (at least 95% of) the alginate beads do not drop more than 5%, often not more than 2% of their original distance as measured from the bottom of the container in which the particular inventive composition was present for a period of at least 4 weeks when maintained in a quiescent state at room temperature.

Evaluation of Viscosity:

The viscosity of the compositions were evaluated utilizing using an LVT-II Brookfield Viscometer, #2 spindle at 20 rpm and 20° C. The viscosity of all of the compositions according to Examples 1–11 was in the range of 1100–1500 cps.

The viscosity of the composition according to Ex. 12 measured as noted above was 306 cps.

Evaluation of Efficacy against Hard Water Stains:

A formulation according to the invention, namely the formulation described as "Ex. 10" on Table 1 was evaluated for its efficacy in removing hard water stains. Such hard water stains are also referred to as "limescale". The test protocol was as follows:

Five sample marble tiles, each measuring 5.75 inches by 2.88 inches by 0.37 inches were washed and dried for one hour in a laboratory oven at 80° C. The tiles were then weighed, and thereafter immersed in 900 ml. of the formulation according to Ex. 10 for 10 seconds, removed from the formulation and thereafter allowed to rest at room temperature (approx. 20° C.) on a laboratory bench. Thereafter the tiles were thoroughly rinsed with deionized water, manually dried using a laboratory wipe (Kimwipe®), and then again dried for one hour at 80° C. in a laboratory oven. Thereafter the tiles were removed, and allowed to cool to room temperature and reweighed. The results of this test, including average results for limescale removal and % weight loss are indicated in the following table.

TABLE 4

| sample tile # | initial weight (g) | final weight (g) | limescale removed (g) | % wt. loss of sample tile |
|---|---|---|---|---|
| 1 | 294.0960 | 294.0490 | 0.0470 | 0.0160 |
| 2 | 293.4320 | 293.3760 | 0.0560 | 0.0191 |
| 3 | 295.4210 | 295.3680 | 0.0530 | 0.0179 |
| 4 | 298.8390 | 298.7870 | 0.0520 | 0.0174 |
| 5 | 304.0830 | 304.0290 | 0.0540 | 0.0178 |
| | | | 0.0524 (avg.) | 0.0176 (avg.) |

The results indicate the loss of carbonates (calcium carbonate, magnesium carbonates, etc.) from the marble compositions of the tiles, and demonstrate the efficacy of the inventive composition in the removal of inorganic carbonates, a major constituent in limescale.

As a comparative example, the same test protocol as indicated above was repeated but using a commercially available bathroom cleaning product, "Lysol® Cling Toilet Bowl Cleaner—Country Scent" instead of the formulation according to Ex. 10. The results of this test are indicated in the following table.

TABLE 4

(comparative example)

| sample tile # | initial weight (g) | final weight (g) | limescale removed (g) | % wt. loss of sample tile |
|---|---|---|---|---|
| 6 | 295.8070 | 295.7960 | 0.0110 | 0.0037 |
| 7 | 296.8830 | 296.8690 | 0.0140 | 0.0047 |
| 8 | 291.8520 | 291.8400 | 0.0120 | 0.0041 |
| 9 | 300.3410 | 300.3370 | 0.0040 | 0.0013 |
| 10 | 299.4050 | 299.3920 | 0.0130 | 0.0043 |
| | | | 0.0108 (avg.) | 0.0036 (avg.) |

As can be seen by comparing the results of the foregoing tables, the sample tiles treated with the inventive composition exhibited good efficacy at removal of inorganic carbonates from the sample tiles, while the tiles treated with the prior art composition demonstrated much lower efficacy at removal of inorganic carbonates.

Evaluation of Antimicrobial Efficacy:

Several of the exemplary formulations described in more detail on Table 1 above were evaluated in order to evaluate their antimicrobial efficacy against *Staphylococcus aurelis* (gram positive type pathogenic bacteria) (ATCC 6538), *Salmonella choleraesuis* (gram negative type pathogenic bacteria) (ATCC 10708), *Escheria coli* (gram negative type pathogenic bacteria) (ATCC 11229) and *Pseudomonas aeruginosa* (ATCC 15442). The testing was performed generally in accordance with the protocols outlined in "Use-Dilution Method", Protocols 955.14, 955.15 and 964.02 described in Chapter 6 of "Official Methods of Analysis", 16$^{th}$ Edition, of the Association of Official Analytical Chemists; "Germicidal and Detergent Sanitizing Action of Disinfectants", 960.09 described in Chapter 6 of "Official Methods of Analysis", 15$^{th}$ Edition, of the Association of Official Analytical Chemists; or American Society for Testing and Materials (ASTM) E 1054-91 the contents of which are herein incorporated by reference. This test is also commonly referred to as the "AOAC Use-Dilution Test Method". Testing was performed on the inventive formulation described as "Ex. 10" described on Table 1, above at dilutions of 1 part formulation to 25 parts water.

As is appreciated by the skilled practitioner in the art, the results of the AOAC Use-Dilution Test Method indicates the number of test substrates wherein the tested organism remains viable after contact for 10 minutes with at test disinfecting composition/total number of tested substrates (cylinders) evaluated in accordance with the AOAC Use-Dilution Test. Thus, a result of "0/60" indicates that of 60 test substrates bearing the test organism and contacted for 10 minutes in a test disinfecting composition, 0 test substrates had viable (live) test organisms at the conclusion of the test. Such a result is excellent, illustrating the excellent disinfecting efficacy of the tested composition.

Results of the antimicrobial testing are indicated on the Table, below. The reported results indicate the number of test cylinders with live test organisms/number of test cylinders tested for each example formulation and organism tested.

TABLE 5

| | Test Results | Conclusion |
|---|---|---|
| *Staphylococcus aureus* | 1/60 | Pass |
| *Salmonella choleraesuis* | 1/60 | Pass |
| *Escheria coli* | 1/60 | Pass |
| *Pseudomonas aeruginosa* | 1/60 | Pass |

As may be seen from the results indicated above, the compositions according to the invention provide excellent cleaning benefits to hard surfaces, including hard surfaces with difficult to remove stains. These advantages are further supplemented by the excellent antimicrobial efficacy of these compositions against known bacteria commonly found in bathroom, kitchen and other environments. Such advantages clearly illustrate the superior characteristics of the compositions, the cleaning and antimicrobial benefits attending its use which is not before known to the art.

The invention claimed is:

1. A hard surface cleaning and/or disinfecting composition which comprises:
   a water soluble organic acid constituent;
   at least one anionic surfactant;
   suspended inclusions which appear as visibly discernible, discrete particulate materials and wherein said inclusions are based on alginate beads;
   a thickener consisting essentially of a constituent;
   optionally, at least one further detersive surfactant selected from nonionic, amphoteric and zwitterionic surfactants;
   optionally, at least one organic solvent;
   optionally, one or more constituents for improving the aesthetic or functional features of the inventive compositions;
   and water; wherein the composition has a pH of 5 or less.

2. The composition according to claim 1 wherein the acid constituent contains an acid selected from the group consisting of: citric acid, sorbic acid, acetic acid, formic acid, maleic acid, adipic acid, lactic acid, malic acid, malonic acid, glycolic acid, and mixtures thereof.

3. The composition according to claim 2 wherein the acid constituent comprises citric acid.

4. The composition according to claim 1 wherein the composition comprises an organic solvent.

5. The composition according to claim 4 wherein the organic solvent is selected from alcohols, glycols, water miscible ethers, water miscible glycol ethers, monalkylether esters, and mixtures thereof.

6. The composition according to claim 5 wherein the organic solvent is selected from alcohols, water miscible glycol ethers and mixtures thereof.

7. The composition according to claim 5 wherein the organic solvent is an alcohol.

8. The composition according to claim 1 wherein the compositions exclude added organic solvents.

9. The composition according to claim 1 wherein the majority of the inclusions do not drop more than 7% of their original distance as measured from the bottom of the container in which the inventive composition is present when they have returned to a quiescent state following manual shaking.

10. The composition according to claim 9 wherein the majority of the inclusions do not drop more than 7% of their original distance as measured from the bottom of the container in which the inventive composition is present when they have returned to a quiescent state following manual shaking when measured after 72 hours when left in a quiescent state at room temperature.

11. The composition according to claim 10 wherein the majority of the inclusions do not drop more than 7% of their original distance as measured from the bottom of the container in which the inventive composition is present when they have returned to a quiescent state following manual shaking when measured after 5 days when left in a quiescent state at room temperature.

12. The composition according to claim 11 wherein the majority of the inclusions do not drop more than 7% of their original distance as measured from the bottom of the container in which the inventive composition is present when they have returned to a quiescent state following manual shaking when measured after 10 days when left in a quiescent state at room temperature.

13. The composition according to claim 12 wherein the majority of the inclusions do not drop more than 7% of their original distance as measured from the bottom of the container in which the inventive composition is present when they have returned to a quiescent state following manual shaking when measured after 14 days when left in a quiescent state at room temperature.

14. The composition according to claim 1 wherein the pH is from about 1 to about 5.

15. The composition according to claim 14 wherein the pH is from about 1 to about 4.

16. The composition according to claim 15 wherein the pH is from about 1 to about 3.

17. The composition according to claim 1 having a viscosity of from about 750 to about 1500 centipoise, as measured at room temperature on a RVT Brookfield viscometer, spindle #2, at 60 rpm.

18. A hard surface cleaning and/or disinfecting composition according to claim 1 wherein said composition exhibits antimicrobial efficacy against at least one of the following organisms: *Staphylococcus aureus* (gram positive type pathogenic bacteria) (ATCC 6538), *Salmonella choleraesuis* (gram negative type pathogenic bacteria) (ATCC 10708), *Escheria coli* (gram negative type pathogenic bacteria) (ATCC 11229) and *Pseudomonas aeruginosa* (ATCC 15442) of not more than 1/60 according to the AOAC Use-Dilution Test Method.

19. A method of treating a hard surface comprising applying an effective amount of a composition according to claim 1 to a surface in need of treatment.

20. A hard surface cleaning and/or disinfecting composition according to claim 1 wherein:
  the thickener constituent consists essentially of one or more cellulose derivatives selected from ethyl cellulose, hydroxy ethyl cellulose, hydroxy propyl cellulose, carboxy methyl cellulose, carboxy methyl hydroxyethyl cellulose, hydroxypropyl cellulose, hydroxy propyl methyl cellulose, and ethyl hydroxy ethyl cellulose.

21. A hard surface cleaning and/or disinfecting composition according to claim 1 wherein the thickener constituent comprises xanthan gum or gellan gum.

* * * * *